(12) United States Patent
Kasukabe et al.

(10) Patent No.: US 6,225,536 B1
(45) Date of Patent: *May 1, 2001

(54) PRODUCTION OF COTTON FIBERS WITH IMPROVED FIBER CHARACTERISTICS

(75) Inventors: Yoshihisa Kasukabe; Koichi Fujisawa; Susumu Nishiguchi; Yoshihiko Maekawa, all of Otsu (JP); Randy Dale Allen, Lubbock, TX (US)

(73) Assignees: Toyo Boseki Kabushiki Kaisha, Osaka-Fu (JP); Texas Tech University, Lubbock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/867,484

(22) Filed: Jun. 2, 1997

Related U.S. Application Data (62) Division of application No. 08/391,696, filed on Feb. 21, 1995, now Pat. No. 5,880,110.

(51) Int. Cl.[7] .............................. A01H 5/00; A01H 5/10; C07H 21/04; C12N 1/21

(52) U.S. Cl. .................. 800/314; 435/252.3; 435/320.1; 536/23.2; 536/24.5; 800/278; 800/286; 800/290; 800/298; 800/317.3

(58) Field of Search .................................. 800/205, 286, 800/290, 294, 298, 306, 314, 317.3; 536/23.6, 24.5; 435/252.2, 252.3, 252.33, 320.1, 419, 468, 469

(56) References Cited

U.S. PATENT DOCUMENTS

| | | | |
|---|---|---|---|
| 4,346,226 | 8/1982 | Thompson et al. | 549/268 |
| 4,591,650 | 5/1986 | Kerb et al. | 549/268 |
| 5,159,135 | * 10/1992 | Umbeck | 800/205 |
| 5,932,713 | * 8/1999 | Kasukabe et al. | 536/23.6 |

OTHER PUBLICATIONS

John M, et al. Gene expression in cotton (*Gossypium hirsutum* L.) fiber: Cloning of the mRNAs. PNAS 89: 5769–5773, Jul. 1992.*

Maniatis et al. Molecular Cloning. A Laboratory Manual, Ch. 9, pp. 1–62 (Cold Spring Harbor, NY), 1989.*

John et al. TIBTECH 10:165–170, May 1992.*

Graves et al. J. Exper. Bot. 39:59–69, Jan. 1988.*

Smith et al. Antisense RNA inhibition of polyglacturonase gene expression in transgenic tomatoes. Nature. 334:724–726, Aug. 1988.*

Zurek et al. Molecular cloning and characteriization of a brassinosteroid–regulated gene from elongating soybean (*Glycine max L.*) epicotyls. Plant Physiology. 104:161–170, 1994.*

Kazuhide Okazawa et al., "Molecular Cloning and cDNA Sequencing of Endoxyloglucan Transferase, a Novel Class of Glycosyltransferase That Mediates Molecular Grafting between Matrix Polysaccharides in Plant Cell Walls," Jun. 30, 1993, The Journal of Biological Chemistry, vol. 268, No. 34, pp. 25364–25368.

J. Huaz Agricultural University, 3, 11(1), pp. 41–47, (1992).

Plant Physiology Communications, 28(1), pp. 15–18, (1992).

Plant Physiology Communications, (5), pp. 31–34, (1988).

Gross et al., J. Plant Growth Regulation, 13:93, 97–99, "Novel Natural Substances Acting in Plant Growth Regulation.", 1994.

* cited by examiner

Primary Examiner—Amy J. Nelson
(74) *Attorney, Agent, or Firm*—Morrison & Foerster LLP (57) ABSTRACT

Methods are disclosed to achieve an improvement in the characteristics and yield of cotton fibers. In one method, a cotton plant of the genus Gossypium in seed form or in growth stage is treated with a brassinosteroid. In another method, an ovule culture is prepared from a cotton plant of the genus Gossypium in a brassinosteroid-containing liquid medium. Cotton fibers with improved fiber characteristics are obtained from the cotton bolls of the treated plant or from the cultured ovules. Also disclosed are a method for inducing specific genes expression in a cotton plant to produce cotton fibers with improved fiber characteristics by treatment with a brassinosteroid, and a cotton plant produced by this method; as well as a novel gene capable of changing the degree of its expression found in the ovules of a cotton plant treated with a brassinosteroid, a gene capable of hybridizing with this novel gene, a recombinant plasmid containing this novel gene, a transformant containing this recombinant plasmid, and the like.

16 Claims, 3 Drawing Sheets

Figure 3:
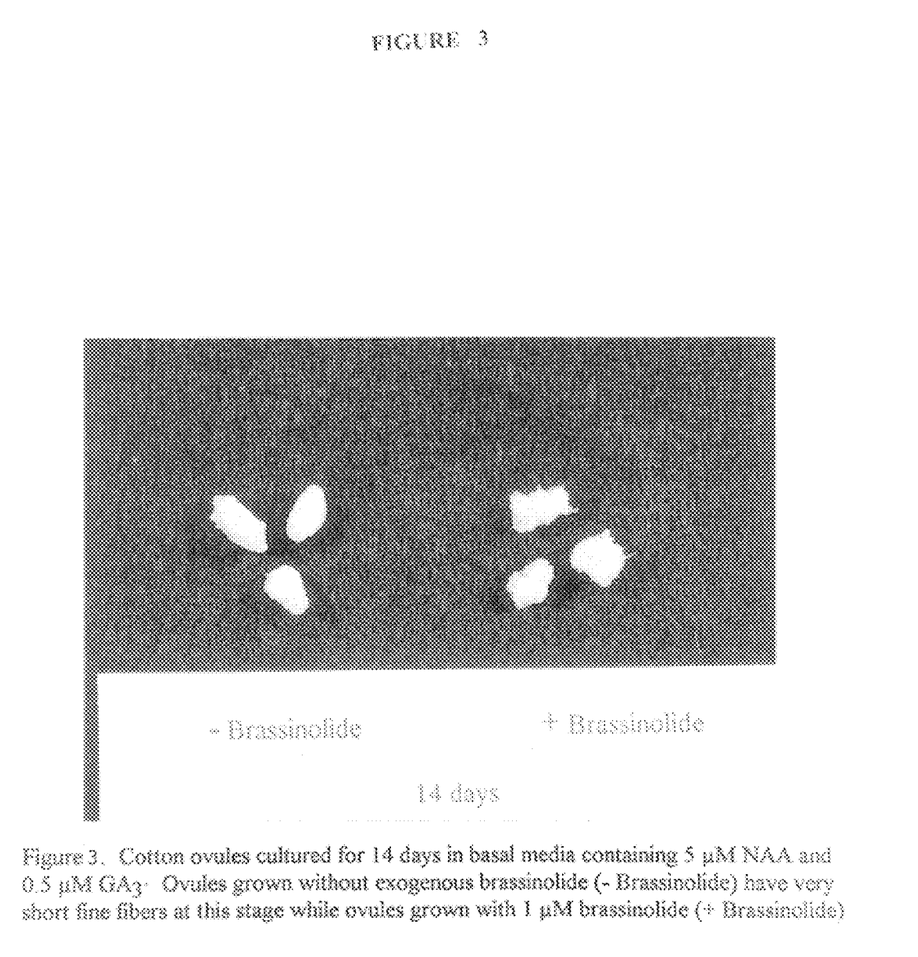
FIG. 3 is a photograph showing the effects of brassinolide treatment on the cotton fibers of Coker 312 (*Gossypium hirstum*).

Figure 3. Cotton ovules cultured for 14 days in basal media containing 5 µM NAA and 0.5 µM GA₃. Ovules grown without exogenous brassinolide (- Brassinolide) have very short fine fibers at this stage while ovules grown with 1 µM brassinolide (+ Brassinolide)

PRODUCTION OF COTTON FIBERS WITH IMPROVED FIBER CHARACTERISTICS

This application is a division of application Ser. No. 08/391,696, filed Feb. 21, 1995, issued as U.S. Pat. No. 5,880,110.

FIELD OF THE INVENTION

The present invention relates to a method for producing cotton fibers with improved fiber characteristics such as increased fiber length, increased fiber fineness and higher fiber strength.

BACKGROUND OF THE INVENTION

Usually, cotton fibers are produced by cultivating a cotton plant of the genus Gossypium and collecting the cotton fibers from the capsules (cotton boils) formed on the cotton plant. There are many varieties of cotton plant, from which cotton fibers with different fiber characteristics can be obtained and used for various applications depending on their fiber characteristics. Cotton fibers are characterized by various properties among which fiber length, fiber fineness and fiber strength are particularly important. Many previous efforts have been made to improve the characteristics of cotton fibers. Attempted improvements have been mainly focused on fiber length and fiber fineness. In particular, there has been a great demand for longer and finer cotton fibers. The variety of cotton plant known as Sea Island is famous for desired fiber characteristics; however, this variety of cotton plant exhibits a poor yield of cotton fibers, therefor the price of Sea Island cotton fibers is very high. If highly yielding cotton plants with fiber characteristics equal to or better than those of Sea Island cotton can be produced, it will be a great contribution to industry.

The methods for improving the characteristics or yield of cotton fibers can be roughly classified into the following three categories:

1. Variety improvement by cross breeding

This method has been utilized most widely so far. At present, almost all the cultivated varieties of cotton plant were bred by this method. However, much time is needed for this method, and because of a limit to the degree of variability, one cannot expect remarkable improvements in fiber characteristics or in yield of cotton fibers.

2. Treatment with plant hormone

Plant hormones such as auxin, gibberellin, cytokinin and ethylene have been widely applied to field crops or horticultural products. Many reports have hitherto been made with respect to the influence of plant hormones on the fiber production of cotton plants, particularly on the fiber elongation mechanism. It is believed that fiber elongation is induced by gibberellin or auxin but inhibited by abscisic acid (Bhardwaj and Sharma, 1971; Singh and Sing, 1975; Baert et al., 1975; Dhindsa et al., 1976; Kosmidou, 1976; Babaev and Agakishiev, 1977; Bazanova, 1977; DeLanghe et al., 1978). Also Beasley and Ting [Amer. J. Bot. 60(2): 130–139 (1973)] have reported that gibberellin has a promoting effect on the fiber elongation in ovule cultures (in vitro) whereas kinetin and abscisic acid have an inhibitory effect on the fiber elongation.

In a field test (in vivo), when non-fertilized flowers of cotton plants were treated with gibberellin just after flowering, there was found a promoting effect on the fiber elongation to a certain degree; in the case of fertilized flowers, however, no significant promotion was caused by gibberellin treatment (The Cotton Foundation Reference Book, Series Number 1, Cotton Physiology, 369, The Cotton Foundation, 1986).

As to the influence of plant hormones on the yield of cotton fibers was analyzed by McCarty and Hedin who reported as follows: a field test on commercial plant growth regulators were conducted for a period of from 1986 to 1992. They found only in the field test of 1992 that an increase in fiber yield was observed with a Foliar Trigger (manufactured by Westbridge Chemical Co.) containing cytokinin or with FPG-5 (manufactured by Baldridge Bio-Research, Inc.) containing cytokinin, indoleacetic acid and gibberelin; however, no significant increase in fiber yield was observed in the other years [J. Agric. Food Chem., 42: 1355–1357 (1994)].

As described above, for the purpose of improving the characteristics and yield of cotton fibers, a number of studies and reports have been made on conventional plant hormones such as auxin, gibberellin, cytokinin and abscisic acid; however, no effect has been fully confirmed yet, and it cannot be said that these plant hormones are effective for practical use.

In recent years, much attention has been paid to brassinosteroids as a novel group of plant hormones, and the action of these hormones on various plants has been studied. For the first time, Micthell, Mandave, et al., discovered brassinolide, which is one of the brassinosteroids, from *Brassica napus* pollen [Nature, 225, 1065 (1970)], and they confirmed that it has a remarkable effect on the cell elongation in the young buds of kidney bean. As described above, brassinolide is one of the steroid compounds with complicated structure, and many compounds with structural similarities thereto have since been discovered from various plants.

The effects of brassinosteroid when applied to cotton plants, was reported by Luo et al., [Plant Physiology Communications, 5:31–34 (1988)] that the treatment of boll stalks with 0.01 or 1 ppm brassinolide reduced the shedding of young bolls in a field test (in vivo). However, no report has hitherto been made that the characteristics or yield of cotton fibers can be improved by use of any brassinosteroid.

For callus culture (in vitro), Wang et al. [Plant Physiology Communications, 28(1): 15–18 (1992)] reported that the addition of 0.01 ppm brassinolide to MS medium induced the callus formation and embryogenesis in cotton plants. However, no report has hitherto been made that the characteristics or yield of cotton fibers can be improved by addition of a brassinosteroid to a medium used for the ovule culture in the production of cotton fibers.

3. Variety improvement by gene recombination technique

In recent years, gene recombinant technique has made starting progress, and several reports have been made on the successful variety improvements in certain kinds of plants (e.g., tomato, soybean) by introduction and expression of a particular gene in these plants to confer a desired genetic trait thereon. If a gene associated with fiber formation and elongation can be introduced into cotton plants and expressed in large quantities, it would become possible to make a remarkable improvement in the characteristics and yield of cotton fibers. At present, however, only the following studies have been made on cotton plants: one is to improve insect resistance by introduction of a gene coding for BT toxin (*Bacillus thuringiensis* produced insecticidal protein toxin), and the other is to improve herbicide (Glyphosate) resistance by introduction of a gene coding for 5-enolpyruvilshikimic acid 3-phosphate synthetase. These attempts result in an improved yield of cotton fibers per unit area but do not contribute to the improvement in the yield of cotton fibers per plant. The mechanism of fiber formation and elongation in cotton plants has not yet been fully elucidated and also very little is now known as to what genes are associated therewith.

SUMMARY OF THE INVENTION

Under these circumstances, the present inventors have intensively studied to improve the characteristics and yield of cotton fibers. As a result, they have found that this problem can be solved by treatment of brassinosteroids, and they have further found a gene associated with the formation and elongation of cotton fibers, thereby completing the present invention.

Thus, the present invention provides methods for producing cotton fibers with improved fiber characteristics, as well as cotton fibers produced by these methods. One method involves treating a cotton plant of the genus Gossypium in seed form or in growth stage with a brassinosteroid, growing the cotton plant to form cotton bolls, and collecting cotton fibers from the cotton bolls of the grown plant. Anther method involves preparing an ovule culture from a cotton plant of the genus Gossypium in a brassinosteroid-containing liquid medium and collecting cotton fibers from the cultured ovules.

The present invention also provides a method for inducing specific genes expression in a cotton plant to produce cotton fibers with improved fiber characteristics, which comprises treating the cotton plant in seed form or in growth stage with a brassinosteroid; as well as a cotton plant produced by this method, and a cotton seed produced by this method.

The present invention further provides a novel gene derived from a cotton plant of the genus Gossypium, capable of changing the degree of its expression by treatment with a brassinosteroid; a gene capable of hybridizing with this novel gene; anti-sense DNA and RNA to this novel gene; a recombinant plasmid containing this novel gene; a transformant containing this recombinant plasmid and a transformed plant.

DETAILED DESCRIPTION OF THE INVENTION

The methods for producing cotton fibers according to the present invention are based on the novel finding that the characteristics and yield of cotton fibers can be improved by treatment of cotton plants with brassinosteroids.

The methods of the present invention can be applied to various varieties of cotton plant, which include, for example, *Gossypium hisutum, Gossypium barbadense, Gossypium arboreum, Gossypium anomalum, Gossypium armourianum, Gossypium klotzchianum* and *Gossypium raimondii*.

The cotton plant to be treated in the methods of the present invention may be in seed form or in growth stage.

The growing cotton plant may be treated in whole or in part. The plant part for treatment is not particularly limited, but is preferably selected from the group consisting of flower buds, flowers, ovules, ovaries, bracts, leaves, stems, roots, boll stalks and young bolls.

The growth stage for treatment, although it is not particularly limited, is preferably a period after flowering, more preferably extending from the 2nd day to the 20th day after flowering.

The brassinosteroids which are used in the methods of the present invention include various compounds with the different steroid skeletons as depicted below.

The compounds of the first type, such as brassinolide (2α,3α,22R,23R-tetrahydroxy-24S-methyl-B-homo-7-oxa-5α-cholestan-6-one), dolicholide, homodolicholide, 24-epibrasinolide and 28-norbrassinolide, have a steroid skeleton of the formula:

For example, brassinolide is represented by the chemical structural formula:

The compounds of the second type, such as castasterone, dolicholsterone, homodolichosterone, homocastasterone, 28-norcastasterone, tiffasterol, teasterol, 24-epicastasterone, 2-epicastasterone, 3-epicastasterone, 3,24-diepicastasterone, 25-methyldolichosterone, 2-epi-25-methyldolichosterone and 2,3-diepi-25-methyldolichosterone, have a steroid skeleton of the formula:

The compounds of the third type, such as 6-deoxocastasterone, 6-deoxo-dolichosterone and 6-deoxyhomodolichosterone, have a steroid skeleton of the formula:

The brassinosteroid may be formulated into any composition form, preferably a liquid, paste, powder or granule formulation. The brassinosteroid concentration is not particularly limited, so long as it is, even if low, effective for the purpose of the present invention. Such a concentration is usually in the range of from $1 \times 10^{-8}$ to 100 ppm, preferably from $1 \times 10^{-6}$ to 50 ppm, and more preferably from $1 \times 10^{-4}$ to 10 ppm.

The composition may further contain any other plant hormone such as auxin, gibberellin, cytokinin or abscisic acid, and if necessary, any conventional additives such as surfactants, emulsifiers, wetting agents and vehicles.

In the case of liquid composition, it may be prepared by dissolving or dispersing a predetermined amount of the brassinosteroid in water. For the purpose of attaining stable effects, auxiliary additives such as emulsifiers, wetting agents and diluents are usually added to the solution or dispersion. It is a general way to prepare a concentrate and dilute it with water to yield a predetermined concentration before use.

A typical example of the concentrate is prepared from the following ingredients: (1) 50% to 98% by weight, preferably 60% to 95% by weight, of a lower aliphatic alcohol such as methanol, ethanol, n-propanol, iso-propanol, n-butanol, iso-butanol or sec-butanol; (2) 1% to 25% by weight, preferably 2% to 20% by weight, of dimethylsulfoxide and an amide polar solvent such as dimethylformamide (DMF), N-methylpyrrolidone (NMP) or dimethylacetamide (DMAA); (3) 1% to 25% by weight, preferably 2% to 20% by weight, of a water-soluble polymer selected from the group consisting of polyalkylene glycols such as polyethylene glycol (PEG), polypropylene glycol and polyethylene glycol; polyvinylpyrrolidone; polyvinyl alcohol; and copolymers thereof; and (4) 0.003 to 1.8 parts by weight, preferably 0.1 to 1.7 parts by weight, based on the total weight of the ingredients (1), (2) and (3) other than water, of a wetting agent selected from the group consisting of polyoxyalkylene ethers such as polyoxyethylene dialkyl ethers, polyoxyethylene alkyl allyl ethers and polyoxyethylene diallyl ether; polyoxyalkylene diesters such as polyoxyethylene dialkyl esters, polyoxyethylene alkyl allyl esters and polyoxyethylene diallyl esters; sulfonates such as sodium dinaphthylmethanesulfonate and calcium lignine-sulfonate dialkylsulfosuccinate.

In the case of a paste composition, it may be prepared by mixing the above liquid composition with a base material such as lanolin or vaseline.

In the case of a powder composition, it may be prepared by mixing the brassinosteroid with an appropriate amount of a solid carrier such as clay, kaoline, talc, diatomaceous earth, silica, calcium, carbonate, monmolinite, bentonite, feldspar, quartz, alumina or sawdust.

In the case of a granule composition, it may be prepared by granulating the above powder composition according to the conventional methods.

The composition of a brassinosteroid thus formulated is used for treatment of a cotton plant in seed form or in growth stage by a spraying, application or immersion technique. As described above, the growing cotton plant may be treated in whole or in part. The plant parts for treatment include flower buds, flowers, ovules, ovaries, bracts, leaves, stems, roots, boll stalks and young bolls.

To maintain the effects of a brassinosteroid, a paste composition prepared by mixing the brassinosteroid with a base material such as lanolin may be applied to the boll stalks or ovaries of a cotton plant. Also, as a method for treatment of a cotton plant with more convenient procedures for a short time, seeds of a cotton plant may be immersed in the composition containing a brassinosteroid dissolved or dispersed in an organic solvent. In general, spraying over the cotton plant in whole is preferred. In particular, direct spraying to the ovaries of a cotton plant in fiber elongation stage between the 2nd day to the 20th day after flowering is still more effective.

The cotton plant thus treated is grown to form cotton bolls, from which the cotton fibers with improved fiber characteristics are collected.

The cotton fibers with improved fiber characteristics can also be obtained by ovule cultures of a cotton plant in a brassinosteroid-containing liquid medium. The ovule cultures can be prepared by the following method.

The liquid medium which can be used is not particularly limited, so long as the ovules of a cotton plant can be grown therein. Such a liquid medium is preferably selected from the group consisting of Murashige-Skoog (MS) medium, Gamborg (B5) medium, Schenk-Hildebrandt (SH) medium, White (W) medium, Linsmaier-Skoog (LS) medium and Beasley-Ting (BT) medium, to which a brassinosteroid is added before use. Particularly preferred is Beasle-Ting (BT) medium.

The amount of the brassinosteroid to be used is not particularly limited, so long as it is a lower concentration to the medium for ovule cultures (in vitro culture system) but effective for the purpose of the present invention. Such a concentration is usually in the range of from $1 \times 10^{-8}$ to 100 ppm, preferably from $1 \times 10^{-6}$ to 50 ppm, and more preferably from $1 \times 10^{-4}$ to 10 ppm.

Further, in addition to the brassinosteroid, other ingredients such as sugars, vitamins and plant hormones are preferably added to the medium. Examples of the plant hormone which can be used are auxin and its analogues such as indoleacetic acid (IAA), naphthaleneacetic acid (NAA), indolebutyric acid (IBA), 2,4-dichlorophenoxyacetic acid (2,4-D); gibberellin ($GA_3$) and its analogues; cytokinins such as kinetin; and abscisic acid. These plant hormones may be used alone or in combination. The concentration of the plant hormone to be added is usually in the range of from 0.005 to 100.0 μM, preferably from 0.05 to 50 μM.

Because the brassinosteroids are hardly soluble in water, they are dissolved in an organic solvent and the solution is then mixed with water before the addition to the medium. Examples of such an organic solvent are lower aliphatic alcohols such as methanol, ethanol and propanol; lower aliphatic ketones such as methyl ethyl ketone and methyl isobutyl ketone; and lower aliphatic ethers such as dimethyl ethers and diethyl ethers.

The ovule cultures can be prepared by the conventional methods, except that a brassinosteroid-containing liquid medium is used.

For example, the ovules of a cotton plant are sterilized with a solution of sodium hypochlorite or the like, and the ovules thus sterilized are aseptically placed on the liquid medium containing a brassinosteroid, followed by stationary incubated. The incubation temperature is usually in the range of from 20° to 40° C., preferably from 25° to 35° C. The cotton fibers with improved characteristics are collected from the ovules thus cultured.

In the present invention, it was observed that the treatment of a cotton plant in seed form or in growth stage with a brassinosteroid according to the above method gave an improvement in the fiber characteristics such as an increase in fiber length. In view of this fact, it is suggested that some particular genes of a cotton plant, which are associated with the formation and elongation of cotton fibers, change remarkably the degree of their expression by treatment with brassinosteroids.

From the cotton plant grown by the above method, the desired genes capable of changing the degree of their expression can be isolated by the differential screening method, subtraction method, differential display method or the like.

As a typical example, the gene isolation by the differential screening method will hereinafter be explained in detail, but such an isolation is not to be construed to limit the scope of the invention.

1. Isolation of genes associated with formation and elongation of cotton fibers (1) Construction of cDNA library First, cotton fibers are separated from the ovules of a cotton plant in the fiber elongation stage. From the separated cotton fibers, poly(A)$^+$RNA is extracted by the ordinary procedures. Using the isolated poly(A)$^+$RNA as a template, single-stranded cDNA is synthesized by reverse transcriptase with oligo(dT) primer. The single-stranded cDNA is converted into a double-stranded cDNA by the polymerase reaction. The double-stranded cDNA is inserted into an appropriate vector, with which host cells such as *Escherichia coli* are transformed, thereby obtaining a cDNA library.

The poly(A)$^+$RNA isolation and cDNA synthesis may also be performed by use of a commercially available cDNA cloning kit. The vector for cDNA library preparation is available from various commercial sources.

(2) Screening of desired genes from cDNA library

The desired genes can be obtained by the differential screening method as follows. The phage plaque pattern of the cDNA library prepared by the above method is replicated onto two filters, each of which is hybridized with either $^{32}$P-labelled cDNA probe prepared from cotton fibers in fiber elongation stage or from cotton fibers in fiber non-elongation state. The cDNA of the desired gene can be selected by detection of a positive hybridization signal only from the cDNA probe of the treated group.

The RNA isolation, cDNA synthesis, DNA digestion, ligation, transformation, hybridization and other techniques necessary for ordinary gene recombination are described in the instructional manuals of commercially available enzymes used for the respective procedures or various text books (e.g., Molecular Cloning edited by Maniatis et al., Cold Spring Harbor, 1989, and Current Protocols in Molecular Biology edited by F. M. Ausubel et al., John Wiley & Sons, Inc., 1987).

The nucleotide sequence of the cloned cDNA can be determined by the Maxam-Gilbert method or the dideoxy chain termination method, each of which is performed by use of a commercially available kit. The nucleotide sequence can also be automatically determined with an autosequencer.

If the cDNA thus analyzed does not correspond to a full-length protein coding sequence, a desired cDNA clone having such a full-length protein coding sequence can be obtained by another plaque hybridization according to the ordinary method, or by the RACE technique.

As an actual example of the gene obtained from cotton fibers in this manner, the nucleotide sequence and deduced amino acid sequence are shown in Sequence Listing, SEQ ID NOs: 1 and 2, respectively. This gene contains a sequence coding for a signal peptide having the ability to effectively pass through the cell wall.

2. Utilization of gene associated with formation and elongation of cotton fibers The genes obtained by the above method can be utilized for mass production of proteins associated with fiber formation and elongation in cotton and other plants.

Further, the DNA sequence coding for a signal peptide may be utilized for modification of cell wall components by expression of various proteins in the cell wall, and such a technique can be applied to the breeding of a novel plant having conferred disease resistance or the like.

For example, a gene associated with fiber formation and elongation may be ligated to an appropriate promoter, followed by introduction into cotton or other plants, which makes it possible to increase the content of a desired protein. In contrast, at least one part of the anti-sense strand (i.e., sequence complementary to the coding sequence) of the above gene may be ligated in reverse direction to an appropriate promoter, followed by introduction into a plant and then expression of the so-called anti-sense RNA, which makes it possible to decrease the content of a desired protein.

Further, the DNA sequence coding for a signal peptide may be ligated to another gene, followed by introduction into a plant, whereby the gene product can be allowed to effectively pass through the cell wall.

The transformation of plants can be performed by electroporation in which protoplasts are treated with electric pulses for introduction of plasmids, or by fusion between protoplasts and small cells, cells, lysosomes or the like. Other methods can also be employed, such as microinjection, polyethylene glycol technique or particle gun technique.

With the use of a plant virus as a vector, a desired gene can also be introduced into a plant. A typical example of the plant virus is cauliflower mosaic virus (CaMV). For example, the introduction of a desired gene is performed as follows. First, a virus genome is inserted in a vector derived from *E. coli* or the like to prepare a recombinant, and a desired gene is inserted in the virus genome. The virus genome thus modified is removed from the recombinant by restriction endonuclease and inoculated into a plant to insert the desired gene into the plant [Hohn et al., Molecular Biology of Plant Tumors, Academic Press, New York, 549–560 (1982), and U.S. Pat. No. 4,407,956].

Further, there is a technique using a Ti plasmid of Agrobacterium. When a plant is infected with bacteria of the genus Agrobacterium, a part of their plasmid DNA is transferred to the plant genome. By making use of such a property, a desired gene can also be introduced into a plant. Upon infection, for example, *Agrobacterium tumefaciens* and *Agrobacterium rhizogenes* induce the formation of crown galls and the formation of hairy roots, respectively. Each of these bacteria has a plasmid designated "Ti-plasmid" or "Ri-plasmid" having T-DNA (transferred DNA) and vir region. The tumor formation is caused by incorporated of T-DNA into the genome of a plant, and then transcription and translation of an oncogene present in the T-DNA in the plant cells. The vir region per se is not transferred to the plant cells, but it is essential to the transfer of T-DNA. Also, the vir region is operable even if it is on another plasmid different from the T-DNA containing plasmid [Nature, 303, 179 (1983)].

If a desired DNA is inserted in the T-DNA on the Ti- or Ri-plasmid, the desired DNA can be incorporated into the plant genome upon infection of the plant with these bacteria of the genus Agrobacterium. In this case, a portion inducing the formation of crown galls or hairy root is removed from the T-DNA of the Ti- or Ri-plasmid without deteriorating the desired transfer function, and the plasmid thus obtained can be used as a vector.

Further, various other vectors can also be used, for example, vectors such as pBI121 (manufactured by Clontech, Co.), which are designated "binary vectors". In this case, the gene associated with fiber formation and elongation is ligated in sense or anti-sense direction to an appropriate promoter, which is inserted in the binary vector, followed by incorporation into a plant. The binary vectors have no vir region, and the bacteria of the genus Agrobacterium to be used for introduction of these vectors are, therefore, required to contain another plasmid having vir region.

These vectors serve as a shuttle vector which can be amplified not only in the bacteria of the genus Agrobacterium but also in E. coli. Accordingly, the recombination of Ti-plasmids can also be performed with E. coli. These vectors have antibiotic-resistance genes, and the screening of transformants can, therefore, be readily done in the transmation of E. coli, bacteria of the genus Agrobacterium, plants or the like. These vectors further have 35S promoter of CaMV, and the gene inserted in these vectors can, therefore, be incorporated into the plant genome and then expressed under no regulatory control.

The following will illustrate the introduction of a desired gene by the bacteria of the genus Agrobacterium into a plant and the regeneration of whole plants from the transformed cells in the case of *Arabidopsis thaliana*.

According to the ordinary method, seeds of *Arabidopsis thaliana* are sowed in MSO plate (Murashige-Skoog inorganic salts, 4.6 g; sucrose, 10 g; 1000×vitamin stock solution, 1 ml/liter, pH 6.2) and aseptically cultivated. The explants of a root are used to prepare callus cultures on CIM plate (prepared by addition of 2,4-dichlorophenoxyacetic acid and kinetin to MSO plate to yield a final concentration of 0.5 µg/ml and 0.05 µg/ml, respectively). A desired gene is ligated to a promoter, which is then inserted in a plasmid having kanamycin-resistance and hygropmycin-resistance genes. The bacteria of the genus Agrobacterium transformed with the plasmid are cultured, and the cultures are diluted and dispensed in appropriate portions in tubes. The root explants in callus form are immersed in these tubes and cocultivated on CIM plate for several days. When the bacterial strains are grown enough to be observed by the naked eye, the root explants are sterilized and then cultivated on SIMC plate (prepared by addition of 2-in, indoleacetic acid and claforan to MSO plate to yield a final concentration of 5 µg/ml, 0.15 µg/ml and 500 µg/ml, respectively) for several days. These explants are finally cultivated on SIMCS plate (prepared by adding kanamycin and hygromycin B to SIMC plate) with a repeated change to a new plate every week.

The transformed explants are continuously grown, and the appearance of calli will be observed. Because of the screening with antibiotics, the color of non-transformed explants changed to brown. The cultivation is continued until the transformants have a size of about 5 mm to form rosettes. When they take the form of a complete rosette, the bottom parts of the transformants are cut with a surgical knife so as not to include any callus, and transplanted on RIM plate (prepared by adding indoleacetic acid to MSO plate to yield a final concentration of 0.5 µg/ml). If the parts cut from the transformants contain a large callus, the roots, even if produced, have a tendency to spread through the callus, and the vascular bundle may, therefore, be often disconnected between the roots and the rosettes. After about 8 to 10 days, these parts are transplanted on a rock wool soaked with inorganic salts medium [5 mM $KNO_3$, 2.5 mM K-phosphate buffer (pH 5.5), 2 mM $MgSO_4$, 2 mM $Ca(NO_3)_2$, 50 µM Fe-EDTA, 1000×microelements (70 mM $H_3BO_3$, 14 mM $MnCl_2$, 0.5 mM $CuSO_4$, 1 mM $ZnSO_4$, 0.2 mM $NaMoO_4$, 10 mM NaCl, 0.01 mM $CoCl_2$) 1 ml/liter].

The plant which has come into flower and then formed siliques is transplanted in the soil soaked with inorganic salts medium, and is grown to give seeds. The seeds are sterilized, sowed in MSH plate (prepared by adding hygromycin B to MSO plate to yield a final concentration of 5 U/ml), and the germinated, thereby obtaining a transformed plant.

From this transformed plant, DNA is extracted according to the ordinary method. The DNA is digested with appropriate endonuclease, and subjected to southern hybridization by use of the gene associated with fiber formation and elongation as a probe. Thus, it can be confirmed whether transformation has occurred in the plant.

Further, from the transformants or non-transformants, RNA is extracted according to the ordinary method, and a probe is prepared which has a sense or anti-sense sequence of the gene associated with fiber formation and elongation. Northern hybridization using these probes makes it possible to examine the degree of expression for the desired gene.

The gene associated with fiber formation and elongation can be expressed specifically in the fiber formation process in cotton fiber cells to make a contribution to fiber elongation. Thus, if the nucleotide sequence of this gene is utilized as a maker for elongation of cotton fibers, the elucidation of fiber elongation mechanism and the isolation of a gene controlling the fiber elongation can be achieved.

With the use of a desired protein necessary for fiber formation and elongation, which also serves as a marker for fiber formation and elongation, it becomes possible to establish a technique of inducing fiber formation and elongation, to elucidate the mechanism of fiber formation and elongation, and to isolate a gene controlling the fiber formation and elongation. The present invention is, therefore, also quite useful in the technique field of cell formation and elongation.

Further, the nuceleotide sequence coding for a protein associated with fiber formation and elongation can be used for gene expression by artificial means such as an in vitro transcription system or with a microorganism such as E. coli to give a protein associated with fiber formation and elongation in large quantities and in pure form. Because the protein thus obtained is a protein associated with fiber formation and elongation, it can be used for modifying the structure of plant cell walls and hence can be useful for the processing of plant raw materials used in the industrial field.

It is believed that the gene of the present invention is a key gene associated with the growth stage of plant cells because it is also associated with fiber formation and elongation. Therefore, for example, by use of cauliflower mosaic virus (CaMV) 35S promoter, all the organs of a plant can be brought into form change over the whole stage of its life cycle. The use of a regulatory promoter for light, heat of wounding makes it possible to prepare a plant capable of changing its form depending upon the growth environment. Further, by use of an organ- or tissue-specific promoter, a form change can be caused only in particular organs or tissues. For example, a promoter capable of causing transcription only at the time of fiber formation can be used for controlling the formation of fibers and causing a modification of fiber characteristics.

According to the present invention, an improvement can be attained in the characteristics (e.g., fiber length, fiber fineness, fiber strength) and yield of cotton fibers. The gene of the present invention can be used to prepare a novel variety of cotton plant having a genetically fixed character of producing cotton fibers with improved fiber characteristics in high yield.

The present invention will be further illustrated by the following Examples, which are not to be construed to limit the scope of the invention.

EXAMPLE 1

Effects of Brassinolide on Fiber Characteristic in Field Cultivation

1. Preparation of brassinosteroid-containing liquid compositions (1) Aqueous solution containing 0.01 ppm brassinolide First, 0.1 mg of brassinolide (manufactured by Fuji Chemical Industries Co., Ltd.) was dissolved in several milliliters of ethanol. Then, 10 liters of water were added to this solution to prepare an aqueous solution of brassinolide having a concentration of 0.01 ppm.

(2) Aqueous solution containing 0.1 ppm brassinolide

First, 1 mg of brassinolide (manufactured by Fuji Chemical Industries Co., Ltd.) was dissolved in several milliliters of ethanol. Then, 10 liters of water were added to this solution to prepare an aqueous solution of brassinolide having a concentration of 0.1 ppm.

(3) Aqueous solution containing 0.5 ppm brassinolide

First, 5 mg of brassinolide (manufactured by Fuji Chemical Industries Co., Ltd.) was dissolved in several milliliters of ethanol. Then, 10 liters of water were added to this solution to prepare an aqueous solution of brassinolide having a concentration of 0.5 ppm.

2. Growth test (conducted on May to November in 1994)

Two cotton plants, Supima (*Gossypium barbadense*) and Ligon Lintless 2 (*Gossypium hirsutum*) which is a mutant variety of cotton plant having little ability to form cotton fibers (both furnished by Dr. Kohel in Southern Crops Res. Lab., USDA-ARS), were used as the test materials. The seeds of both cotton plants were sowed in a nursery bed on May 11, 1994, and the seedlings were transplanted in a test field two weeks after the germination. These cotton plants began flowering on Jul. 15, 1994, and the spraying treatment was performed by spraying the above brassinolide-containing aqueous solution with a hand sprayer over the ovaries and their neighborhood of the cotton plants everyday for a period extending from the 2nd day to the 20th day after the flowering (corresponding to the fiber elongation stage).

At the 50th day to the 60th day after flowering, the ovaries (cotton bolls) were opened. After drying, the ovules were harvested, and cotton fibers were separated from the seeds and evaluated for fiber characteristics.

The evaluation of Supima cotton fibers was achieved by (i) measurements of fiber length, fiber strength and fiber fineness with the 900 HVI system (manufactured by Spinlab Co.) and by (ii) measurements of fiber length by the sorter method and of fiber strength by the Pressley method. The results are shown in Tables 1 and 2.

TABLE 1

EFFECTS OF BRASSINOLIDE TREATMENT ON CHARACTERISTICS OF SUPIMA COTTON FIBERS AS MEASURED BY 900 HVI SYSTEM

| Agent | Concentration (ppm) | Fiber length (inch) | Fiber strength (g/tex) | Fiber fineness (µg/inch) |
|---|---|---|---|---|
| Untreated | 0 | 1.421 ± 0.019 | 47.604 ± 3.362 | 4.309 ± 0.086 |
| Brassinolide | 0.01 | 1.463 ± 0.024 | 49.402 ± 2.268 | 4.255 ± 0.067 |
| Brassinolide | 0.1 | 1.455 ± 0.015 | 50.373 ± 3.231 | 4.507 ± 0.069 |
| Brassinolide | 0.5 | 1.507 ± 0.019 | 52.133 ± 2.329 | 4.548 ± 0.040 |

TABLE 2

EFFECTS OF BRASSINOLIDE TREATMENT ON CHARACTERISTICS OF SUPIMA COTTON FIBERS AS MEASURED BY SORTER AND PRESSLEY METHODS

| Agent | Concentration (ppm) | Fiber length (inch) | Fiber strength (1000 Lbs/in$^2$) |
|---|---|---|---|
| Untreated | 0 | 1.480 ± 0.042 | 108.050 ± 1.717 |
| Brassinolide | 0.01 | 1.503 ± 0.021 | 114.914 ± 5.149 |
| Brassinolide | 0.1 | 1.534 ± 0.026 | 111.783 ± 2.616 |
| Brassinolide | 0.5 | 1.570 ± 0.031 | 120.150 ± 1.863 |

From the results of Tables 1 and 2, it is evident that the fiber length, fiber strength and fiber fineness of cotton fibers were all remarkably increased by the spraying treatment of cotton plants with aqueous solutions of brassinolide. An increase was also observed to a certain extent in the yield of cotton fibers.

On the other hand, the evaluation of Ligon lintless 2 cotton fibers was achieved by visual observation with the naked eye. The results are shown in FIGS. 1 (ovules) and 2 (divided ovules).

Figure 1:
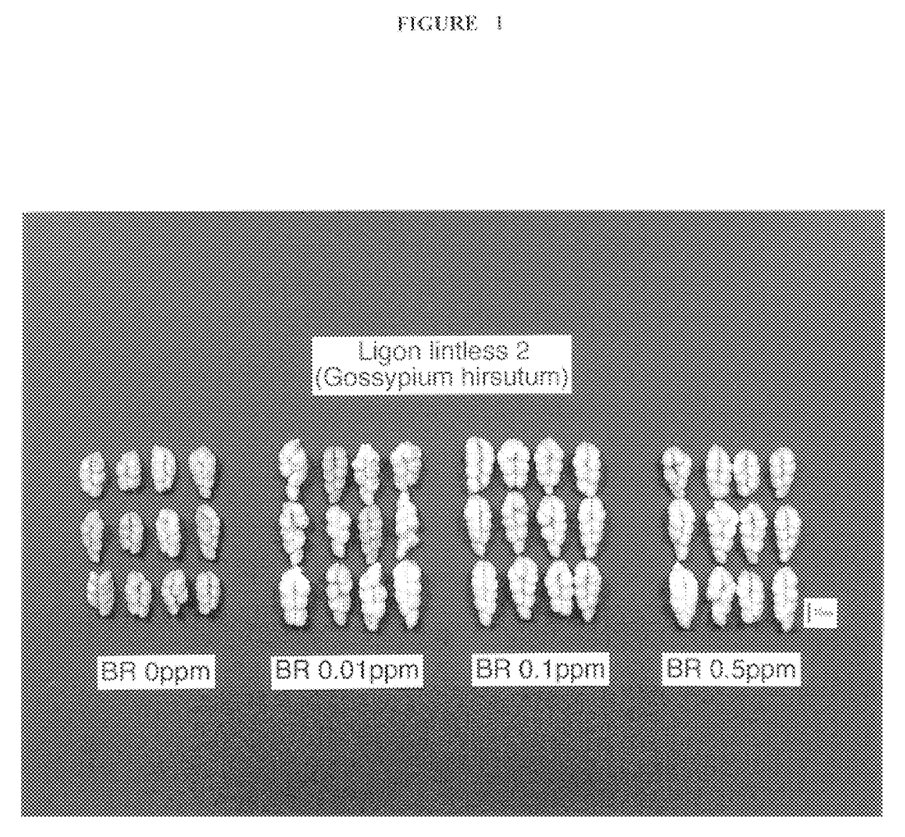
FIG. 1 is a photograph showing the effects of brassinolide treatment on the cotton fibers (ovules) of Ligon lintless 2 (*Gossypium hirsutum*).
Figure 2:
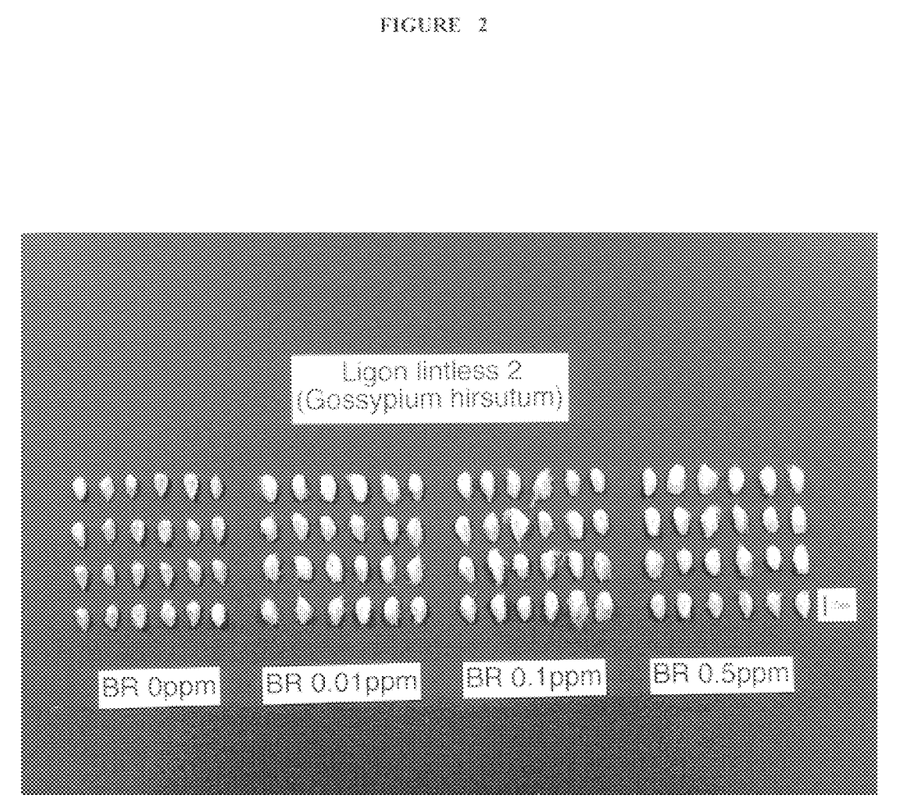
FIG. 2 is another photograph showing the effects of brassinolide treatment on the cotton fibers (divided ovules) of Ligon lintless 2 (*Gossypium hirsutum*).

As can be seen from FIGS. 1 and 2, the yield of cotton fibers was increased even in Ligon lintless 2 which is a mutant variety of cotton plant having little ability to form cotton fibers.

EXAMPLE 2

1. Preparation of brassinosteroid-containing liquid compositions

In the formulation of each liquid composition, symbols for abbreviation have the following meanings:

BR: brassinolide

DMF: dimethylformamide

PEG 1000: polyethylene glycol (M.W., 1000)

EtOH: ethanol

Neoesterin (manufactured by Kumiai Chemical Co., Ltd.)

According to the following formulations, mixtures A, B and C for treatment were prepared.

| Ingredients | Amounts |
|---|---|
| (1) Mixture A (blank) | |
| DMF | 5 g |
| PEG 1000 | 5 g |
| Neosterin (wetting agent) | 10 g |
| EtOH | 10 g |
| Total | 100 g |
| (2) Mixture B (0.05 ppm BR) | |
| BR | 2.5 mg |
| DMF | 5 g |
| PEG 1000 | 5 g |
| Neosterin (wetting agent) | 10 g |
| EtOH | 80 g |
| Total | 100 g |
| (3) Mixture C (0.3 ppm BR) | |
| BR | 15 mg |
| DMF | 5 g |
| PEG 1000 | 5 g |
| Neosterin (wetting agent) | 10 g |
| EtoH | 80 g |
| Total | 100 g |

2. Preparation of brassinosteroid-containing liquid compositions

Using these mixtures, the following liquid compositions containing brassinolide at different concentrations.

(1) Liquid composition containing no brassinolide
The mixture A was 500-fold diluted with water, and this dilution was used.

(2) Liquid composition containing 0.05 ppm brassinolide
The mixture B was 500-fold diluted with water, and this dilution was used.

(3) Liquid composition containing 0.3 ppm brassinolide
The mixture C was 500-fold diluted with water, and this dilution was used.

3. Growth test (conducted May to November in 1994)
In the same manner as described in Example 1, test fields and tested plants were separately provided, and the growth test was conducted. The spraying treatment of cotton plants with different brassinolide-containing liquid compositions was performed in the same manner as described in Example 1.

At the 50th day to the 60th day after flowering, the ovaries (cotton bolls) were opened. After drying, the ovules were harvested, and cotton fibers were separated from the seeds and evaluated for fiber characteristics. The results are shown in Table 3.

TABLE 3

EFFECTS OF BRASSINOLIDE TREATMENT ON CHARACTERISTICS OF SUPIMA COTTON FIBERS AS MEASURED BY 900 HVI SYSTEM

| Agent | Concentration (ppm) | Fiber length (inch) | Fiber strength (g/tex) | Fiber fineness ($\mu$g/inch) |
|---|---|---|---|---|
| Untreated | 0 | 1.411 ± 0.022 | 46.871 ± 3.125 | 4.223 ± 0.082 |
| Brassinolide | 0.05 | 1.475 ± 0.017 | 50.201 ± 2.511 | 4.497 ± 0.052 |
| Brassinolide | 0.3 | 1.498 ± 0.020 | 51.522 ± 2.146 | 4.538 ± 0.030 |

From the results of Table 3, it is evident that the fiber length, fiber strength and fiber fineness of cotton fibers were all remarkably increased by the spraying treatment of cotton plants with liquid compositions of brassinolide containing a surfactant and a wetting agent.

EXAMPLE 3

1. Preparation of brassinosteroid-containing paste composition

In the formulation of each paste composition, symbols for abbreviation have the following meanings:
BR: brassinolide
NMP: N-methylpyrrolidone
EtOH: ethanol According to the following formulations, lanolin pastes A and B for treatment were prepared.

| Ingredients | Amounts |
|---|---|
| (1) Lanolin paste A (blank) | |
| NMP | 0.2 ml |
| EtOH | 19.8 g |
| Dehydrated lanolin | 180 g |
| Total | 200 g |
| (2) Lanolin paste B (0.1 ppm BR) | |
| BR | 20 $\mu$g |
| NMP | 0.2 ml |
| EtOH | 19.8 g |
| Dehydrated lanolin | 180 g |
| Total | 200 g |

2. Growth test (conducted on May to November in 1994)
In the same manner as described in Example 1, test fields and tested plants were separately provided, and the growth test was conducted. The treatment of cotton plants was started by application of the above lanolin pastes to the boll stalks of cotton plants on the 2nd day after flowering.

At the 50th day to the 60th day after flowering, the ovaries (cotton bolls) were opened. After drying, the ovules were collected, and cotton fibers were separated from the seeds and evaluated for fiber characteristics. The results are shown in Table 4.

TABLE 4

EFFECTS OF BRASSINOLIDE TREATMENT ON CHARACTERISTICS OF SUPIMA COTTON FIBERS AS MEASURED BY 900 HVI SYSTEM

| Agent | Concentration (ppm) | Fiber length (inch) | Fiber strength (g/tex) | Fiber fineness ($\mu$g/inch) |
|---|---|---|---|---|
| Untreated | 0 | 1.412 ± 0.021 | 48.221 ± 2.175 | 4.290 ± 0.067 |
| Brassinolide | 0.1 | 1.449 ± 0.011 | 49.892 ± 2.143 | 4.501 ± 0.032 |

From the results of Table 4, it is evident that the fiber length, fiber strength and fiber fineness of cotton fibres were all remarkably increased by the application treatment of cotton plants with a brassinolide-containing paste composition.

EXAMPLE 4

Effects of Brassinolide on Fiber Length in Ovule Cultures

Two varieties of cotton plants, Ligon lintless 2 (*Gossypium hirstum*) and Coker 312 (*Gossypium hirstum*), were cultivated in a test field. The ovaries at the 2nd day after flowering were collected, from which the sepals, bracts and petals were removed. The ovaries thus separated were sterilized by immersion in 70% ethanol for 30 seconds, and further sterilized by immersion in an aqueous solution containing 10 wt % sodium hypochlorite and 0.05 wt % Tween 20 for 20 minutes. The ovules were aseptically taken from the ovaries using a sterile pincette, and placed in an Erlenmeyer flask which had been charged with 50 ml of liquid media formulated as shown in Table 5 and then sterilized by autoclaving, followed by suspension culture at 32° C.

TABLE 5

MEDIUM FORMULATION

| Ingredients | Formulation 1 | Formulation 2 |
| --- | --- | --- |
| Potassium dihydrogenphosphate | 2.0 mM | 2.0 mM |
| Boric acid | 0.1 mM | 0.1 mM |
| Sodium molybdate | 0.001 mM | 0.001 mM |
| Calcium chloride | 3.0 mM | 3.0 mM |
| Potassium iodide | 0.0005 mM | 0.0005 mM |
| Cobalt chloride | 0.0001 mM | 0.0001 mM |
| Magnesium sulfate | 2.0 mM | 2.0 mM |
| Manganese sulfate | 0.1 mM | 0.1 mM |
| Zinc sulfate | 0.03 mM | 0.03 mM |
| Copper sulfate | 0.0001 mM | 0.0001 mM |
| Potassium nitrite | 50.0 mM | 50.0 mM |
| Ferric sulfate | 0.03 mM | 0.03 mM |
| Disodium EDTA | 0.03 mM | 0.03 mM |
| Nicotinic acid | 0.004 mM | 0.004 mM |
| Pyridoxine hydrochloride | 0.004 mM | 0.004 mM |
| Thiamine hydrochloride | 0.004 mM | 0.004 mM |
| Myoinositol | 1.0 mM | 1.0 mM |
| D-Glucose | 100.0 mM | 1000 mM |
| D-Fructose | 20.0 mM | 20.0 mM |
| Indoleacetic acid | 5.0 $\mu$M | 5.0 $\mu$M |
| Gibberellin | 0.5 $\mu$M | 0.5 $\mu$M |
| Brassinolide | 1.0 $\mu$M | 0 $\mu$M |
| pH | 6.8 | 6.8 |

The ovalues cultured on the medium of formulation 1 (containing brassinolide) were referred to as the treated group, while those cultured on the medium of formulation 2 (containing no brassinolide) were referred to as the control group.

1. Ligon lintless 2 (*Gossypium hirstum*)

After culture for 30 days, the fiber length of Ligon lintless 2 cotton fibers was measured. The measurement of fiber length was performed as follows. First, cotton fibers were taken from the ovules using a finely-tapered pincette. Because the cotton fibers thus taken were composed of interwined filaments, they were separated into the respective filaments. The filaments were microscopically confirmed, and the fiber length was measured with a ruler for every 100 filaments obtained from the respective groups. The fiber length of the filaments from the ovules was 1.98±0.27 cm in the treated group and 1.70±0.19 cm in the control filed. Further, the ovules at the 30th day after the culturing were sufficiently dried at room temperature, and cotton fibers were taken from the dried ovules, followed by measurement of fiber weight per ovule. The fiber weight was 8.85 mg in the treated group and 7.02 mg in the control group.

2. Coker 312 (*Gossypium histum*)

The effects of brassinolide were also examined with respect to Coker 312. From the flasks of both groups, the respective ovules at the 14th day after the culturing were taken and compared with each other. An increase in the yield of cotton fibers was clearly observed by the naked eye. The results are shown in FIG. 3.

Then, 15 ovules at the 30th day after the culturing were taken in each group, from which cotton fibers were separated, followed by measurement of fiber length. The fiber length was 3.60±0.36 cm in the treated group and 2.60±0.28 cm in the control group, indicating that the filaments in the treated group was about 25% longer than those in the control group. In another experiment conducted in the same manner as described above, the fiber length was 4.10±0.5 cm in the treated group and 2.80±0.5 cm in the control group, indicating the filaments in the treated group were about 30% longer than those in the control group.

In view of these results, it is clear that the fiber length and fiber yield can be both increased by addition of brassinolide to a medium for ovule cultures of cotton plants.

EXAMPLE 5

Cloning of Gene Associated With Formation of Cotton Fibers

1. Preparation of poly(A)$^+$RNA

The cotton plants, Supima (*Gossypium barbadense*), cultivated in a field was used as the test material. The ovules at the 5th day to the 15th day after flowering (fiber elongation stage) and those at the 25th day to the 30th day after the following (fiber non-elongation stage) were collected, and cotton fibers were separated from the respective seeds. About 5 g of the cotton fibers thus obtained were immediately frozen in liquid nitrogen and pulverized with a mortar in the presence of liquid nitrogen. Then, 10 ml of 0.2M Tris-acetate buffer for extraction [containing 5M guanidinethiocyanate, 0.7% β-mercaptoethanol, 1% polyvinylpyrrolidone (M.W., 360,000) and 0.62% sodium N-lauroylsarcosinate, pH 8.5] was added, and the mixture was pulverized with a polytron homengenizer (manufactured by KINEMATICA Co.) under ice cooling for 2 minutes. At that time, β-mercaptoethanol and polyvinylpyrrolidone were added to the buffer just before use. The pulverized mixture was centrifuged at 17,000×g for 20 minutes, and the supernatant was collected.

The supernatant was filtered through a miracroth, and the filtrate was gently overlaid on 1.5 ml of 5.7M aqueous cesium chloride in a centrifuge tube, followed by centrifugation at 155,000×g for 20 hours at 20° C. The supernatant was discarded, and the precipitated RNA was collected. The precipitate was dissolved in 3 ml of 10 mM Tris-HCl and 1 mM EDTA-2Na, pH 8.0 (referred to TE buffer), to which an equal volume of a mixture of phenol, chloroform and isoamyl alcohol (volume ratio, 25:24:1) was added. The mixture was centrifuged at 17,000×g for 20 minutes, and the upper aqueous layer was collected. To the aqueous layer, a 0.1-fold volume of 3M aqueous sodium acetate (adjusted to pH 6.2 by addition of gracious acetic acid) and a 2.5-fold volume of ethanol were added, and the mixture was well agitated and allowed to stand at −20° C. overnight. Then, the mixture was centrifuged at 17,000×g for 20 minutes, and the precipitate was washed with 70% ethanol and dried in vacuo.

The dry product was dissolved in 500 $\mu$l of TE buffer to give a solution of the whole RNA. This RNA solution was incubated at 65° C. for 5 minutes and immediately cooled on ice, to which an equal volume of 3×coupling buffer (10 mM Tris-HCl, 5 mM EDTA-2Na, 1M NaCl,0.5% SDS, pH 7.5) was added. The mixture was overlaid on an oligo-dT cellulose column (manufactured by Clontcch, Co.) which had been equilibrated with equilibration buffer (100 mM Tris-HCl, 5 mM EDTA-2Na, 0.5M NaCl, 0.5% SDS, pH 7.5).

The column was washed with an about 10-fold volume of the equilibration buffer, and the poly(A)+RNA was eluted with elution buffer (10 mM Tris-HCl, 5 mM EDTA-2Na, pH 7.5).

To the eluate obtained, a 0.1-fold volume of the 3M aqueous sodium acetate and a 2.5-fold volume of ethanol were added, and the mixture was allowed to stand at −70° C. Then, the mixture was centrifuged at 10,000×g, and the precipitate was washed with 70% ethanol and dried in vacuo. The dry product was dissolved again in 500 μl of TE buffer, and the purification was repeatedly conducted with an oligo-dT cellulose column. The poly(A)+RNA from the fiber elongation stage was used for preparation of a cDNA library and a cDNA probe for differential screening, and the poly(A)+RNA from the fiber non-elongation stage was used for preparation of a cDNA probe for differential screening.

2. Preparation of cDNA library specific to fiber elongation stage

The cDNA library was prepared with ZAP-cDNA Synthesis Kit (manufactured by Stratagene Co.). The poly(A)+ RNA from the fiber elongation stage obtained in paragraph 1 as a template, and double-stranded cDNA was synthesized by reverse transcriptase with oligo(dT)primer according to the method of Gubler and Hoffman et al. [Gene, 25, 263–269 (1983)].

To both ends of the cDNA obtained, EcoRI adaptors (each having XhoI and SpeI sites in the inside) were ligated, and the ligates DNA was digested with XhoI. Then, the fragment was ligated between the EcoRI and XhoI sites of the λ phage vector, λ ZAPII arm, and the vector was packaged with an in vitro packaging kit (manufactured by Stratagene Co., GIGAPACK Gold), followed by infection into E. coli strain SURE ($OD_{660}$=0.5), which afforded a number of recombinant λ phages serving as the cDNA library specific to the fiber elongation stage. This cDNA library had a size of 5.0×10$^6$.

3. Preparation of probes

The poly(A)+RNA prepared from the cotton fibers at the 15th day in the fiber elongation stage or in the fiber non-elongation stage was used as a template, cDNA was synthesized by reverse transcriptase M-MLV (manufactured by Toyobo Co., Ltd.) with oligo(dT) primer. After the synthesis, alkali treatment was performed to remove the poly(A)+RNA by hydrolysis. The cDNA thus obtained was used as a template, and a $^{32}$P-labelled probe was prepared with Random Primed DNA Labeling Kit (manufactured by USB Co.).

The $^{32}$P-labelled probes thus prepared by the cDNA from the fiber elongation stage and by the cDNA from the fiber non-elongation stage were used as a positive probe and as a negative probe, respectively, for differential screening.

4. Screening of gene associated with fiber formation and elongation

The above pharges constituting the cDNA library in the fiber elongation stage were infected into E. coli cells, which were grown on LB agar medium. About 50,000 pieces of pharge DNA were replicated on two nylon membranes (Hybond-N, manufactured by Amersham Co.).

The nylon membranes having replicated pharge DNA thereon were transferred on a filter paper containing a solution for alkali denaturation (0.5M NaOH, 1.5M NaCl) and allowed to stand for 4 minutes. Then, the nylon membranes were transferred on a filter paper containing a solution for neutralization (0.5M Tris-HCl, 1.5M NaCl, pH 8.0) and allowed to stand for 5 minutes. After washing with 2×SSC (0.3M NaCl, 0.03M trisodium citrate), these membranes were subjected to DNA fixation with Stratalinker (manufactured by Stratagene Co.). The membranes thus treated for DNA fixation were prehybridized in hybridization buffer [50% formamide, 0.5% SDS, 6×SSPE (3M NaCl, 0.2M NaH$_2$PO$_4$, 20 mM EDTA-2Na, pH 7.4), 5×Denhardt solution (0.1% Ficoll, 0.1% polyvinylpyrrolidone, 0.1% bovine serum albumin), 50 μg/ml denatured salmon sperm DNA] at 42° C. for 3 hours, and the cDNA probes prepared in paragraph 3 were separately added to the respective membranes, followed by hybridization at 42° C. for 20 hours. After that, the membranes were removed and washed with solutions each containing 2×SSC, 1×SSC, 0.5×SSC or 0.1×SSC at 42° C. for 1 to 2 hours. These membranes were dried and exposed overnight to X-ray films by allowing to closely adhere thereto.

As a result, 34 positive clones capable of hybridizing more strongly with the positive probe (from the fiber elongation stage) than with the negative probe (from the fiber non-elongation stage) were selected. The analysis was conducted for one of these positive colones, which was designated KC22.

KC22 has a partial homology with the gene of soybean exhibiting brassinosteroid-regulated protein (BRU1) [D. M. Zurek and S. D. Clouse, Plant Physiol (ROCKV) 102, 132 (1993)]; the gene coding for xyloglucan transferase of Vigna angularis, Glycine max or the like [Nishitani et al., J. Bio. Chem., 268, 25364–25368 (1993)]; and the meri-5 gene exhibiting specific expression to the apical meristem of Arabidopsis [J. I. Medford, J. S. Elmer, and H. J. Klee, Plant Cell, 3, 359–370 (1991)]. The xyloglucan transferase is an enzyme catalyzing the bridge transfer of xyloglucan which is the main component of plant cell walls, and it is, therefore, believed to be a key enzyme associated with cell wall elongation.

Further, Northern analysis was performed using RNA isolated from the brassinolide-treated group and the control group, and it was found that KC22 is regulated by brassinolide.

From the phage DNA of KC22, plasmid clone pKC22 having a cDNA insert was prepared by the in vivo excision method with ZAP-cDNA Synthesis Kit (manufactured by Stratagene Co.).

First, 200 μl of a KC22-containing phage solution was mixed with 200 μl of E. coli XL1-Blue suspension and 1 μl of helper phage R408 suspension, and the mixture was incubated at 37° C. for 15 minutes, to which 3 ml of 2×YT medium was added. Shaken cultures were grown at 37° C. for 2 hours and treated at 70° C. for 20 minutes, followed by centrifugation at 4000×g for 10 minutes, and the supernatant was collected.

Then, 30 μl of the supernatant was mixed with 30 μl of E. coli SOLR suspension, and the mixture was incubated at 37° C. for 15 minutes and inoculated on several microliters of LB agar medium containing 50 ppm ampicillin, followed by incubation at 37° C. overnight. The colony-forming E. coli contained the plasmid clone pKC22 having the cDNA insert.

The nucleotide sequence of the cDNA insert in the plasmid pKC22 was determined by the dideoxy chain termination method [Messing, Methods in Enzymol., 101, 20–78 (1993)]. The nucleotide sequence and deduced amino acid sequence are shown in the Sequence Listing, SEQ ID NOs: 1 and 2, respectively. These sequences correspond to the cDNA nucleotide sequence and amino acid sequence, respectively, of a gene capable of changing the degree of its expression at the time of fiber formation and elongation.

5. Expression of desired gene in E. coli

The transformants obtained above were suspended in 50 ml of LB medium containing 100 μg/ml of ampicillin, and shaken cultures were grown at 37° C. When the turbity $OD_{660}$ of the shaken cultures became 0.2, isopropyl-β-D-thiogalactopyrenosido (IPTG) was added to yield a final concentration of 10 mM. The shake cultures were further grown at 37° C. until the turbidity $OD_{660}$ became 1.0. After completion of the culturing, bacterial cells were collected by centrifugation at 1600×g for 15 minutes. The collected bacterial cells were suspended in a 4-fold volume of lysis buffer [50 mM Tris-HCl (pH 8.0), 1 mM EDTA-2Na, 1 μM PMSF (phenylmethylsulfonyl fluoride), 10% sucrose], to which Lysozyme (manufactured by Sigma Co.) was added to yield a final concentration of 1 mg/ml, followed by allowing to stand on ice for 10 minutes. After 10 minutes, Nonidet P-40 (manufactured by Sigma Co.) was added to the cell suspension to yield of a final concentration of 1%, and the mixture was further allowed to stand on ice for 10 minutes, followed by centrifugation at 48,000×g for 1 hour. To the supernatant obtained, an equal volume of 2×Laemli sample buffer [0.125M Tris-HCl (pH 6.8), 20% glycerol, 10% β-mercaptoethanol, 6% SDS, 0.1% bromophenol blue] was added, and the mixture was boiled for 2 minutes, followed by SDS-polyacrylamide gel electrophoresis (SDS-PAGE). After completion of the electrophoresis, the gel was stained with Coomassie brilliant blue (CBB) and decolorized with 7% acetic acid and 25% methanol. A band was observed near the position corresponding to the molecular weight of 39 kDa as desired, and the expression of the desired gene was thus confirmed.

6. Preparation of Arabidopsis thaliana transformant (1) Construction of plasmid The nucleotide sequence of KC22 as shown by SEQ ID NO: 1 was digested with DraI so as to contain the whole open reading frame thereof. The DraI fragment was subcloned in the SmaI site of pUC10. This plasmid was digested with SalI and HindIII, in which the HindIII-XhoI fragment of 35S promotor was subcloned. This clone was digested with HindIII and SacI, and the HindIII-SacI fragment was subcloned between the HindIII site and the SacI site of binary vector pBI101-Hm2. The plasmid thus obtained was designated pBI35S-22. The construction of this plasmid is shown in FIG. 4. The transformed E. coli JM109 was designated E. Coli JM109/pBI35S-22.

(2) Introduction of plasmid into Agrobacterium

The E. coli pBI35S-22 obtained in paragraph 6(1) and the E. coli strain HB101 containing helper plasmid pRK2013 were separately cultured on LB medium containing 50 mg/l of kanamycin at 37° C. overnight, while the Agrobacterium strain EHA101 was cultured on LB medium containing 50 mg/l of kanamycin at 37° C. over two successive nights. Then, bacterial cells were harvested by taking 1.5 ml of each of the cultures in an Eppendorf tube, and then washed with LB medium. These bacterial cells were suspended in 1 ml of LB medium, after which three kinds of bacteria were mixed together in 100 μl portions. The mixture was plated on LB agar medium and incubated at 28° C. for ensuring the conjugation transfer of plasmids to Agrobacterium. After 1 to 2 days, a part of the medium was scratched by means of a sterile loop, and spread over LB agar medium containing 50 mg/l kanamycin, 20 mg/l hygromycin B and 25 mg/l chloramphenicol. The incubation was continued at 28° C. for 2 days, and a single colony was selected. The transformant thus obtained was designated EHA101/pBI35S-22.

(3) Cultivation of sterile Arabidopsis thaliana

Several dozens of seeds of Arabidopsis thaliana stain Wassilewskija (hereinafter referred to as strain WS; furnished by Dr. Shinmyo in Osaka University) were placed in a 1.5-ml tube, to which 1 ml of 70% ethanol was added, and the seeds were allowed to stand for 3 minutes. The seeds were immersed in a solution for sterilization (5% sodium hypochlorite, 0.02% Triton X-100) for 3 minutes, washed five times with sterile water, and then sowed in MSO plate (4.6 g of Murashige-Skoog inorganic salts, 10 g of sucrose, 1 ml/liter 1000×vitamin stock solution, pH 6.2). This plate was allowed to stand at 4° C. for 2 days for low-temperature treatment and then cultivated at 22° C. in a plant incubator (model MLR-350HT, manufactured by Sanyo Electric Co., Ltd.) under long-day conditions (16 hours light and 8 hours dark) at a light intensity of 6000 lux for 21 days. To increase the infection efficiency, the plants were aseptically pulled out and allowed to spread their roots on a fresh MSO plate, followed by cultivation for 2 days.

(4) Infection with Agrobacterium

The roots of several pieces of the above strain WS cultivated for 21 days were gathered together, cut with a surgical knife to have a uniform length of about 1.5 to 2.0 cm, and placed in order on CIM plate (prepared by adding 2,4-dichlorophenoxyacetic acid and kinetin to MSO plate to yield a final concentration of 0.5 μg/ml and 0.05 μg/ml, respectively). These root explants were cultivated under long-day conditions (16 hours light and 8 hours dark) at a light intensity of 3000 lux for 2 days. MS diluent (6.4 g/liter Murashige-Skoog inorganic salts, pH 6.3) was 3-fold diluted and dispensed in 1 ml portions into tubes, in which the roots in callus form were immersed for 10 minutes. These explants were placed in order on two layers of sterile filter papers to remove excess water, transferred on fresh CIM plate, and cocultivated for 2 days under the same conditions as described above.

(5) Sterilization

The explants grown to a degree enough to observe the respective bacterial strains with the naked eye were placed in a solution for sterilization (prepared by adding claforan to MS diluent to yield a final concentration of 200 μg/ml), followed by washing with gentle shaking for 60 minutes. After five repetitions of this operation, these explants were placed on a sterile filter paper to remove water, placed in order on SIMC plate (prepared by adding 2-ip, IAA and claforan to MSO plate to yield of a final concentration of 5 μg/ml, 0.15 μg/ml and 500 μg/ml, respectively), and cultivated under long-day conditions (16 hours light and 8 hours dark) at a light intensity of 6000 lux for 2 days.

(6) Selection of transformed plants

The above explants cultivated for 2 days were transplanted on SIMCS plate (prepared by adding hygromycin B to SIMC plate to yield a final concentration of 4.6 U/ml) and cultivated under long-day conditions (16 hours light and 8 hours dark) at a light intensity of 6000 lux. Thereafter, these explants were transplanted on fresh SIMCS plate every week. The transformed explants were continuously grown to become dome-shaped swollen calli, while the color of non-transformants changed to brown. The calli of the transformants exhibited green color after about 2 weeks. After about 1 month, leaves were formed and then became rosettes.

(7) Regeneration of transformed plants

The bottom parts of the plants in rosette form were cut with a razor or a surgical knife so as not to include any callus, and slightly inserted into RIM plate as if they were placed thereon. After 8 to 10 days, the plant having several roots of about 1 to 2 cm in length was transplanted with a pincette in a mini-pot of rock wool (manufactured by NITTO BOSEKI CO., LTD) soaked with inorganic salts medium [5 mM $KNO_3$, 2.5 mM K-phosphate buffer (pH 5.5), 2 mM $MgSO_4$, 2 mM $Ca(NO_3)_2$, 50 μM Fe-EDTA, 1000×microelements (70 mM $H_3BO_3$, 14 mM $MnCl_2$, 0.5 mM $CuSO_4$, 1 mM $ZnSO_4$, 0.2 mM $NaMoO_4$, 10 mM NaCl, 0.01 mM $CoCl_2$) 1 ml/liter], and cultivated. After flowering and podding, these plants were transplanted in the soil which was prepared by mixing pearlite and vermiculite (manufactured by TES Co.) at a ratio of 1:1 and soaking in inorganic salts medium. After about 1 month, a few hundred of seeds per plant were obtained. These seeds are hereinafter referred to as T1 seeds.

(8) Acquisition of antibiotic-resistant strains

About one hundred T1 seeds were sterilized by the same method as described in paragraph 6(3), and then sowed in MSH plate. Hygromycin B-resistant strains were germinated at a ratio of approximately 3:1.

7. DNA extraction and southern hybridization

The above germinated T1 seeds were transplanted with a pincette in a mini-pot of rock wool soaked with inorganic salts medium, and cultivated at 22° C. under long-day conditions (16 hours light and 8 hours dark) at a light intensity of 6000 lux. After 2 weeks, the aerial parts of the plants were cut with a surgical knife as if the surface of the rock wool was smoothed with a knife, and immediately frozen with liquid nitrogen. The frozen aerial parts were finely pulverized with a mortar in the presence of liquid nitrogen, to which 3 ml of DNA extraction buffer [200 mM Tris-HCl (pH 8.0), 100 mM EDTA-2Na, 1% sodium N-lauroylsarcosinate, 100 μg/ml proteinase K] was added, and the mixture was well agitated and then incubated at 60° C. for 1 hour, followed by centrifugation at 10,000×g for 10 minutes. The supernatant was filtered through a miracloth, and the filtrate was transferred in a new tube. After three extractions with a mixture of phenol, chloroform and isoamyl alcohol (25:24:1), ethanol precipitation was performed. The precipitate was dissolved in TE buffer. From about 2.0 g of the plants, 20 μg of genomic DNA was obtained. Each 1 μg of genomic DNA was digested with EcoRI and HindIII, and the DNA fragments were subjected to 1% agarose electrophoresis and southern hybridization.

In the same manner as described, the non-transformed seeds of the WS strain were germinated and grown, after which DNA isolated from the plants was digested with EcoRI and HindIII, and the DNA fragments were subjected to 1% agarose gel electrophoresis and southern hybridization. As the probe for hybridization, pKC22 was used.

The southern hybridization was performed according to the method described in Molecular Cloning, A Laboratory Manual, ch. 9, pp. 31–58 (Cold Spring Harbor, 1989). That is, each DNA sample was subjected to 1% agarose gel electrophoresis, followed by alkali denaturation and overnight southern blotting on a nylon membrane (Hybond-N, manufactured by Amersham Co.). The membrane was irradiated with an UV trans-illuminator (254 nm) for 3 minutes to cause DNA fixation. This membrane was prehybridized in 5 ml of prehybridization buffer [5×Denhardt solution, 6×SSC, 0.1% SDS, 10 μg/ml salmon sperm DNA] at 50° C. for 2 hours, followed by hybridization with a probe at 50° C. overnight. The membrane was washed twice with a washing solution containing 2×SSC and 0.1% SDS at room temperature for 10 minutes and then twice with the same solution at 50° C. for 30 minutes. After the membrane was dried, autoradiograms were prepared by exposing the membrane to an X-ray film (manufactured by Eastman Kodak Co.) in a cassette to at −80° C. overnight. Comparison of signal patterns detected by southern hybridization was made among: (i) the non-transformants; (ii) the transformants having pKC22; and (iii) the transformants having only the vector.

Specific signals from the transformants (ii) were observed at positions of about 1.6 and 0.7 kbp for the EcoRI-digested sample and at a position of about 6 kbp for the HindIII-digested sample, in addition to endogenous signals common to (i), (ii) and (iii), indicating that the desired gene was incorporated in the transformants (ii).

What is claimed is:

1. An isolated gene from ovules or fibers of a cotton plant, wherein the level of expression of said gene is changed by treatment with a brassinosterioid, wherein said gene is expressed during the formation or elongation of cotton fibers, and wherein said gene encodes the amino acid sequence of SEQ ID NO:2.

2. The gene according to claim 1, wherein said gene has the nucleotide sequence of SEQ ID NO:1.

3. An isolated gene that is expressed during the formation or elongation of cotton fibers, and that hybridizes to the gene of claim 1 under the following conditions:
   (i) hybridization in 50% formamide, 0.5% SDS, 6×SSPE, 5×Denhardt's solution, and 50 μg/ml denatured salmon sperm DNA at 42° C.; and
   (ii) wash in 0.1×SSC at 42° C., wherein the level of expression of said gene is changed by treatment with a brassinosteroid.

4. An isolated anti-sense DNA to the gene of claim 3.

5. An isolated anti-sense RNA to the gene of claim 3.

6. A recombinant plasmid comprising the gene of claim 3 or an anti-sense sequence to said gene.

7. A microorganism transformed with a recombinant plasmid comprising the gene of claim 3 or an anti-sense sequence to said gene.

8. The microorganism according to claim 7, wherein the microorganism is selected from the group consisting of *Escherichia coli* and Agrobacterium.

9. A plant transformed with a recombinant plasmid comprising the gene of claim 3 or an anti-sense sequence to said gene.

10. The plant according to claim 9, wherein the plant is selected from the group consisting of *Arabidopsis thaliana*, cotton and tobacco.

11. A cotton plant transformed with a recombinant plasmid comprising the gene of claim 3 or an anti-sense sequence to said gene.

12. A cotton seed from the cotton plant of claim 11.

13. A cotton fiber from the cotton plant of claim 11.

14. The cotton plant according to claim 11, wherein the cotton plant is selected from the group consisting of *Gossypium hirsutum, Gossypium barbadense, Gossypium arboreum, Gossypium anomalum, Gossypium armourianum, Gossypium klotzchianum* and *Gossypium raimondii*.

15. A method for producing a transformed plant, which comprises transforming a host cell of a plant with a recombinant plasmid comprising the gene of claim 3 or an anti-sense sequence to said gene, resulting in a transformed host cell; and regenerating a transformed plant from the transformed host cell.

16. A method for producing cotton fibers, which comprises transforming a host cell of a cotton plant with a recombinant plasmid comprising the gene of claim 3 or an anti-sense sequence to said gene, resulting in a transformed host cell; regenerating a transformed cotton plant from the transformed host cell; cultivating the transformed cotton plant to produce cotton bolls; and collecting cotton fibers from the cotton bolls.

* * * * *

```
                          SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
         (A) LENGTH: 1035 base pairs
         (B) TYPE: nucleic acid
         (C) STRANDEDNESS: double
         (D) TOPOLOGY: linear (ii) MOLECULE TYPE: cDNA to mRNA (vi) ORIGINAL SOURCE:
         (A) ORGANISM: Gossypium barbadense
         (F) TISSUE TYPE: cotton fibers (vii) IMMEDIATE SOURCE:
         (A) LIBRARY: elongating fiber tissue-derived cDNA library
         (B) CLONE: KC22

(ix) FEATURE:
         (A) NAME/KEY: Coding Sequence
```

(B) LOCATION: 32...898
        (D) OTHER INFORMATION:
        (A) NAME/KEY: mRNA
        (B) LOCATION: 1...1035
        (D) OTHER INFORMATION:
        (A) NAME/KEY: 5'UTR
        (B) LOCATION: 1...31
        (D) OTHER INFORMATION: 3'UTR (899 to 1035)

(xi) SEQUENCE DESCRIPTION: SEQ ID NO:1:

```
CAATAATTCT CTCTGTTTCT CTGGTTTAAA C ATG GGT ATG GGT TTA AGG AAT              52
                                 Met Gly Met Gly Leu Arg Asn
                                  1               5

GGA TTT CTT TTG ATT TTA TCT TGT GTT GTT ACA CTT TCC CTC TCA GTT            100
Gly Phe Leu Leu Ile Leu Ser Cys Val Val Thr Leu Ser Leu Ser Val
         10                  15                  20

TTG GGG CGA CCT GCC ACT TTC CTT GAA GAT TTT AGA ATC ACT TGG TCT            148
Leu Gly Arg Pro Ala Thr Phe Leu Glu Asp Phe Arg Ile Thr Trp Ser
 25                  30                  35

GAT TCT CAT ATT AGG CAA ATC GAT GGA GGG AGA GCC ATC CAA CTT GTT            196
Asp Ser His Ile Arg Gln Ile Asp Gly Gly Arg Ala Ile Gln Leu Val
40                  45                  50                  55

CTC GAC CAA AAT TCA GGC TGT GGA TTT GCT TCT AAA AGG CAG TAT TTG            244
Leu Asp Gln Asn Ser Gly Cys Gly Phe Ala Ser Lys Arg Gln Tyr Leu
                 60                  65                  70

TTC GGA CGT GTC AGC ATG AAA ATC AAG CTC ATC CCC GGC GAC TCC GCC            292
Phe Gly Arg Val Ser Met Lys Ile Lys Leu Ile Pro Gly Asp Ser Ala
             75                  80                  85

GGA ACA GTC ACC GCC TTT TAT ATG AAT TCT GTT ACA GAT GCT GTG CGA            340
Gly Thr Val Thr Ala Phe Tyr Met Asn Ser Val Thr Asp Ala Val Arg
         90                  95                 100

GAT GAG CTA GAC TTC GAG TTC TTG GGA AAC CGT ACC GGG CAG CCA TAT            388
Asp Glu Leu Asp Phe Glu Phe Leu Gly Asn Arg Thr Gly Gln Pro Tyr
    105                 110                 115

ACG GTT CAA ACC AAT ATC TAT GCC CAT GGA AAG GGT GAC AGG GAA CAA            436
Thr Val Gln Thr Asn Ile Tyr Ala His Gly Lys Gly Asp Arg Glu Gln
120                 125                 130                 135

AGG GTT AAC CTT TGG TTC GAT CCT GCT GCA GAT TTC CAT ACT TAC TCA            484
Arg Val Asn Leu Trp Phe Asp Pro Ala Ala Asp Phe His Thr Tyr Ser
                140                 145                 150

ATC ATG TGG AAC CAT CAT CAG ATT GTG TTC TAT ATT GAT GAA GTG CCA            532
Ile Met Trp Asn His His Gln Ile Val Phe Tyr Ile Asp Glu Val Pro
            155                 160                 165

ATT AGG GTT TAT AAG AAC AAT GAA GCT AGA AAT ATC CCA TAC CCA AAA            580
Ile Arg Val Tyr Lys Asn Asn Glu Ala Arg Asn Ile Pro Tyr Pro Lys
        170                 175                 180

CTC CAG CCA ATG GGA GTT TAT TCA ACG CTG TGG GAG GCT GAT GAT TGG            628
Leu Gln Pro Met Gly Val Tyr Ser Thr Leu Trp Glu Ala Asp Asp Trp
185                 190                 195

GCA ACA AGG GGA GGT TTA GAG AAA ATT GAT TGG ACC AAA GCT CCG TTC            676
Ala Thr Arg Gly Gly Leu Glu Lys Ile Asp Trp Thr Lys Ala Pro Phe
200                 205                 210                 215

TTA GCT TAT TAC AAG GAC TTC GAC ATT GAA GGA TGT CCG GTT CCA GGG            724
Leu Ala Tyr Tyr Lys Asp Phe Asp Ile Glu Gly Cys Pro Val Pro Gly
                220                 225                 230

CCA GTA AAC TGT GCC ACA AAC AGT AGG AAC TGG TGG GAG GGC ACT GCT            772
Pro Val Asn Cys Ala Thr Asn Ser Arg Asn Trp Trp Glu Gly Thr Ala
            235                 240                 245

TAT CAA GCC CTT AAT GCC ATG GAA GCT AAA AGA TAT AGT TGG GTT CGT            820
Tyr Gln Ala Leu Asn Ala Met Glu Ala Lys Arg Tyr Ser Trp Val Arg
        250                 255                 260
```

```
ATG AAC CAC GTG ATA TAC GAT TAC TGC ACC GAC AAG TCC CGT TAC CCG      868
Met Asn His Val Ile Tyr Asp Tyr Cys Thr Asp Lys Ser Arg Tyr Pro
    265                 270                 275

GTT ACC CCA CCG GAG TGC ATG TCC ATC ATC TGAAAATCCA AACCCAAGTG AAG     921
Val Thr Pro Pro Glu Cys Met Ser Ile Ile
280                 285

TTTCGTGTCC TATTTTACGT ACATATGTAC CTCCCTTTAT ACAAATAATA GAGCCATGCA     981

AAAATTGGGT TTTAAAAAAA AAAAAAAAAA AAAAAAAAAA AAAAAAAAAA AAAA          1035
```

(2) INFORMATION FOR SEQ ID NO:2:

(i) SEQUENCE CHARACTERISTICS:
        (A) LENGTH: 289 amino acids
        (B) TYPE: amino acid
        (C) STRANDEDNESS: single
        (D) TOPOLOGY: linear     (ii) MOLECULE TYPE: protein     (v) FRAGMENT TYPE: internal     (xi) SEQUENCE DESCRIPTION: SEQ ID NO:2:

```
Met Gly Met Gly Leu Arg Asn Gly Phe Leu Leu Ile Leu Ser Cys Val
1               5                   10                  15

Val Thr Leu Ser Leu Ser Val Leu Gly Arg Pro Ala Thr Phe Leu Glu
                20                  25                  30

Asp Phe Arg Ile Thr Trp Ser Asp Ser His Ile Arg Gln Ile Asp Gly
            35                  40                  45

Gly Arg Ala Ile Gln Leu Val Leu Asp Gln Asn Ser Gly Cys Gly Phe
        50                  55                  60

Ala Ser Lys Arg Gln Tyr Leu Phe Gly Arg Val Ser Met Lys Ile Lys
65                  70                  75                  80

Leu Ile Pro Gly Asp Ser Ala Gly Thr Val Thr Ala Phe Tyr Met Asn
                85                  90                  95

Ser Val Thr Asp Ala Val Arg Asp Glu Leu Asp Phe Glu Phe Leu Gly
                100                 105                 110

Asn Arg Thr Gly Gln Pro Tyr Thr Val Gln Thr Asn Ile Tyr Ala His
            115                 120                 125

Gly Lys Gly Asp Arg Glu Gln Arg Val Asn Leu Trp Phe Asp Pro Ala
        130                 135                 140

Ala Asp Phe His Thr Tyr Ser Ile Met Trp Asn His His Gln Ile Val
145                 150                 155                 160

Phe Tyr Ile Asp Glu Val Pro Ile Arg Val Tyr Lys Asn Asn Glu Ala
                165                 170                 175

Arg Asn Ile Pro Tyr Pro Lys Leu Gln Pro Met Gly Val Tyr Ser Thr
            180                 185                 190

Leu Trp Glu Ala Asp Asp Trp Ala Thr Arg Gly Gly Leu Glu Lys Ile
        195                 200                 205

Asp Trp Thr Lys Ala Pro Phe Leu Ala Tyr Tyr Lys Asp Phe Asp Ile
210                 215                 220

Glu Gly Cys Pro Val Pro Gly Pro Val Asn Cys Ala Thr Asn Ser Arg
225                 230                 235                 240

Asn Trp Trp Glu Gly Thr Ala Tyr Gln Ala Leu Asn Ala Met Glu Ala
```

```
                         245                      250                      255
Lys Arg Tyr Ser Trp Val Arg Met Asn His Val Ile Tyr Asp Tyr Cys
            260                      265                      270

Thr Asp Lys Ser Arg Tyr Pro Val Thr Pro Pro Glu Cys Met Ser Ile
            275                      280                      285

Ile
```